US005466249A

United States Patent [19]
de Putter

[11] Patent Number: 5,466,249
[45] Date of Patent: Nov. 14, 1995

[54] OPERATING LAMP DEVICE

[76] Inventor: Cornelis de Putter, Mozartlaan 53, 3603 BE Maarssen, Netherlands

[21] Appl. No.: 166,708

[22] Filed: Dec. 13, 1993

[30] Foreign Application Priority Data

Dec. 15, 1992 [NL] Netherlands .......................... 9202166

[51] Int. Cl.[6] .................................................... A61N 5/06
[52] U.S. Cl. ............................ 607/90; 362/130; 362/131
[58] Field of Search ............... 607/88–95; 362/130–131

[56] References Cited

U.S. PATENT DOCUMENTS

| | | | |
|---|---|---|---|
| 1,684,081 | 9/1928 | Akers | 607/90 X |
| 2,611,367 | 9/1952 | Harkenrider | 607/90 |
| 2,637,322 | 5/1953 | Clay | 607/90 |
| 3,818,217 | 6/1974 | Hetz . | |

FOREIGN PATENT DOCUMENTS

| | | | |
|---|---|---|---|
| 0422331 | 8/1990 | European Pat. Off. . | |
| 1240623 | 5/1967 | Germany . | |
| 3118028 | 11/1982 | Germany | 607/88 |
| 5220233 | 8/1993 | Japan | 607/89 |

*Primary Examiner*—Angela D. Sykes
*Attorney, Agent, or Firm*—Kane, Dalsimer, Sullivan, Kurucz, Levy, Eisele and Richard

[57] ABSTRACT

In an operating lamp device comprising a light source a guiding apparatus for the light source is provided which has a stationary position relative to the operating table or treatment chair for directing a light beam towards a certain treatment area and keeping it there. The guiding apparatus offers the light source a spherical cap-shaped area of movement of which the center of curvature coincides with the respective treatment area of a patient. The guiding apparatus might be attached to a movable back support or neck support, but might also be attached to a carrier not mechanically coupled to the operating table or treatment chair. In the latter case control signals generate a motion of the carrier in correspondence with a motion of the operating table or treatment chair.

8 Claims, 2 Drawing Sheets

OPERATING LAMP DEVICE

BACKGROUND OF THE INVENTION

The invention relates to an operating lamp device comprising a light source and means for directing a light beam emitted by said light source towards a pre-determined treatment area of a patient lying on an operating table or sitting in a treatment chair and for maintaining the light beam on said treatment area during a movement of said operating table or treatment chair.

Such an operating lamp device is known from DE-A-3.227.494. In this known apparatus rather complicated measures have been taken to provide a movement for said light source, such that its light beam remains directed towards the respective treatment area. Moreover, for accomplishing the movement of the light source moreover complicated computing measures have been taken.

It is an object of the invention to provide an operating lamp device of the present type, using which the goal, maintaining the light beam on the treatment area, may be reached in a less complicated way.

Thus, according to the invention, the operating lamp device is characterised in that the means comprise a guiding apparatus for the light source, which basically has a stationary position relative to the operating table or treatment chair and which offers to said light source a spherical cap-shaped area of movement, wherein the centre of curvature of the spherical cap coincides with the treatment area of the patient.

As a result of the spherical cap-shaped area of movement of the light source the light beam always will be directed towards the respective treatment area irrespective the position of the light source. Because the guiding apparatus basically has a stationary position relative to the operating table or treatment chair a movement of the operating table or treatment chair will lead to a corresponding movement of the guiding apparatus, such that the position of the light source relative to the treatment area of the patient will not change.

In a preferred embodiment of the device according to the invention the guiding apparatus is attached to a movable back support or neck support of the operating table or treatment chair.

Because the guiding apparatus is attached to a movable back support or neck support the operating lamp device is extremely fit for use with dental treatments. For, in this case the mouth of the patient will be the treatment area and its position is principally defined by the back support or neck support, repectively, of a treatment chair. When the neck support or back support is moved relative to the remaining section of the treatment chair the guiding apparatus automatically will move along, such that the light beam remains directed on the mouth of the patient.

Further, in correspondence with the invention, a preferred embodiment is mentioned, wherein the guiding apparatus is attached to a separate carrier not mechanically coupled with the operating table or treatment chair, said carrier being movable in correspondence with the movement of the operating table or treatment chair under influence of control signals generated by motion sensors in said operating table or treatment chair.

Just as with the previously mentioned embodiment there exists a coupling between the position of the operating table or treatment chair (for example the position of its movable back support or neck support) and the position of the guiding apparatus, and thus the light source. Now however this coupling is not realised in a mechanical way but in a not-mechanical way, for example using electric sensors. Due to the absence of a mechanical coupling between the operating table or treatment chair, respectively, and the guiding apparatus one can avoid, that vibrations of the operating table or treatment chair, as occur for example during medical treatments, are transferred to the guiding apparatus and the light source, leading to disturbing motions of the light source and the light beam.

Further it is preferred, that the guiding apparatus is adjustable relative to the operating table or treatment chair. This adjustability of the guiding apparatus is intended to allow for directing the light beam to the respective treatment area before treating a new patient. For example, this adjustability may occur in the longitudinal direction of the operating table or treatment chair, respectively, transversely thereto and mainly perpendicularly to the plane of the operating table or treatment chair, respectively. Using such an adjustability one further may take into account different body dimensions of patients. Once adjusted the guiding apparatus however defines the mentioned spherical cap-shaped area of movement, in the centre of curvature of which is positioned the treatment area of the patient.

Further it may be advantageous if the guiding apparatus is able to be moved away, such a to be pivoted away, from the operating table or treatment chair. Through moving away the guiding apparatus it for example can be made easier for a patient to step in or out of a treatment chair, without being hindered by the guiding apparatus.

Constructively several possibilities exsist for realising a guiding apparatus according to the invention. So a constructively favourable embodiment is mentioned, according to which the guiding apparatus comprises a first arc-shaped guide extending transversally to the longitudinal direction of the operating table or treatment chair and a second arc-shaped guide movable along said first arc-shaped guide and extending into the longitudinal direction of the operating table or treatment chair, wherein the light source is able to move along said second arc-shaped guide.

In combination both arc-shaped guides define a spherical cap along which the light source may be moved, and of which the centre of curvature coincides with the respective treatment area of the patient.

When, in correspondence with another embodiment of the operating lamp device according to the invention, the light source is provided with proximity switches for causing a motion of the light source along the guiding apparatus, a displacement of the light source along the guiding apparatus may be realised without any physical contact between the operator and the light source. Thus any risk of contamination is prevented. For example, a displacement of the light source along the guiding apparatus might be needed to change the angle of attack of the light beam at the treatment area.

When the light source is adjustable relative to the guiding apparatus along a radian of the spherical cap, the distance between the light source and the treatment area may be changed, such as to change the light intensity at the treatment area.

Finally it is possible, that the light source is automatically movable along the guiding apparatus dependent upon the position of the operating table or treatment chair. An example thereof is an automatic displacement of the light source dependent upon the inclination of a neck support or back support, respectively, of a treatment chair. When the back support or neck support encloses a large angle with the remaining section of a treatment chair, such that the treated patient more or less sits up, it relates mostly to a medical treatment in the lower jaw of the patient; this will lead to a corresponding angle of attack of the light beam. If however, the angle between the back support or neck support and the remaining section of the treatment chair is small, and the patient is substantially lying, this generally indicates a treatment of the upper jaw of the patient. In such a case the light beam should reach the treatment area from another direction. Due to the automatic adjustment of the light source along the guiding apparatus now such a displacement of the light source is provided automatically dependent upon the angle of inclination between the back support or neck support, respectively, and the remaining section of the treatment chair. In a way, the treatment chair deduces from the angle of inclination whether it relates to a treatment at the lower jaw or at the upper jaw of the patient.

BRIEF DESCRIPTION OF THE DRAWINGS

Hereinafter the invention will be elucidated further referring to the drawing, in which a number of embodiments of the operating lamp device according to the invention is illustrated.

DETAILED DESCRIPTION OF THE DRAWINGS

Figure 1:
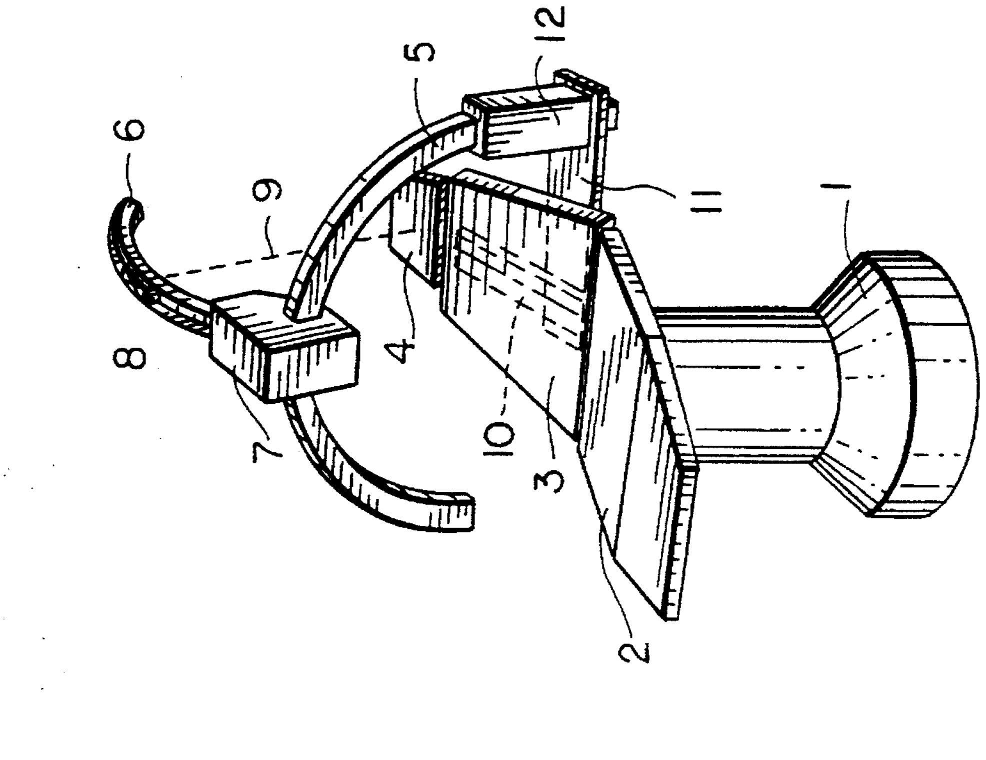
FIG. 1 illustrates schematically and in a perspective view a first embodiment of the operating lamp device according to the invention.

In FIG. 1 a treatment chair, for example for dental treatments, is illustrated having a base 1, a support section 2 movable upwards and downwards relative to the base 1 by means not shown further and a back support 3 pivotable relative to the support section 2. Further at the side of the back support 3 facing away from the support section 2 a neck support 4 is provided.

A guiding apparatus is attached to the back support 3 comprising as most important features a first arc-shaped guide 5 extending transversally to the longitudinal direction of the treatment chair, and a second arc-shaped guide 6 extending into the longitudinal direction of the treatment chair. By means of an only schematically indicated slide 7 the second arc-shaped guide 6 is able to move along the first arc-shaped guide 5. The second arc-shaped guide 6 itself carries a second slide 8 which is able to move along the second arc-shaped guide and which carries a light source not shown. The light beam emitted by said light source has been indicated schematically by a dotted line 9.

It is noted, that instead of a second slide 8, which is able to move along the second arc-shaped guide 6, it is also possible to stationary attach the light source to the second arc-shaped guide 6, whereas this second arc-shaped guide is slideable relative to the slide 7 along an arc. The resulting motion of the light source however corresponds with the motion, which will be obtained with the embodiment illustrated in FIG. 1.

Together both arc-shaped guides 5 and 6 define a spherical cap-shaped area of movement for the light source. The centre of curvature of this spherical cap-shaped area of movement should then coincide with a treatment area of a patient sitting in the treatment chair. Assuming for example, that this treatment area coincides with the neck support 4 of the treatment chair a movement of the second slide 8 along the second arc-shaped guide 6, a movement of the slide 7 along the first arc-shaped guide 5 or a combination of these movements will lead to such a displacement of the light source, that the light beam 9 still is directed to the same treatment area (thus in this case the neck support 4), however that the angle of attack at the treatment area will be changed.

The motion of the second slide 8 along the second arc-shaped guide 6 and the motion of the first slide 7 along the first arc-shaped guide 5 may be realised by the application of proximity switches on the light source, which for example will react on the presence of the hand of the operator. Like this the displacement of the light source may occur without any physical contact between the practising individual and the light source, thus avoiding any risk of contamination. For driving the slides all known means may be used, which will not be elucidated further here.

In correspondence with the invention the previously mentioned guiding apparatus is directly attached to the back support 3 of the treatment chair in the embodiment shown in FIG. 1. For attaining this a longitudinal guide 10 is provided at the rearward side of the back support 3 in which, adjustable into the longitudinal direction of the treatment chair, an arm 11 is provided. The arm 11 carries a height adjustment guide 12, housing an adjustable straight end of the first arc-shaped guide 5. By adjusting the arm 11 along the longitudinal guide 10 and/or adjusting the first arc-shaped guide 5 in height relative to the height adjustment guide 12 the centre of curvature of the spherical cap-shaped area of movement (as being defined by both arc-shaped guides 5 and 6) may be centred at the respective treatment area of a patient.

Once such a centring operation has been carried out a light beam 9 remains directed onto this treatment area during any displacement of the light source along the guiding apparatus, as has been elucidated previously. For directing the light beam onto a new treatment area, or when a patient having different body dimensions takes place into the treatment chair, a new adjustment operation of the guiding apparatus may occur using the longitudinal guide 11 and the height adjustment guide 12.

In addition to the longitudinal adjustment and height adjustment it principally is imaginable too that the guiding apparatus is able to be adjusted transversally to the treatment chair, for example when the height guide 12 is adjustable along arm 11.

It is noted, that a motion of the treatment chair, such as relative to the base 1 moving the support section 2 upward or downward or pivoting the back support 3 relative to said support section 2, does not influence the position of the light source relative to the treatment area. Thus an automatic adaptation is carried out in correspondence with the motion of the treatment chair.

At the previously described embodiment it has been assumed, that only the motion of the back support 3 relative to the support section 2 is important; therefore the guiding apparatus is coupled with this back support. However it is conceivable too, that instead the guiding apparatus is in a corresponding way coupled to the neck support 4, for example if it can move relative to the back support 3. The principle of the device does not change.

Figure 2:
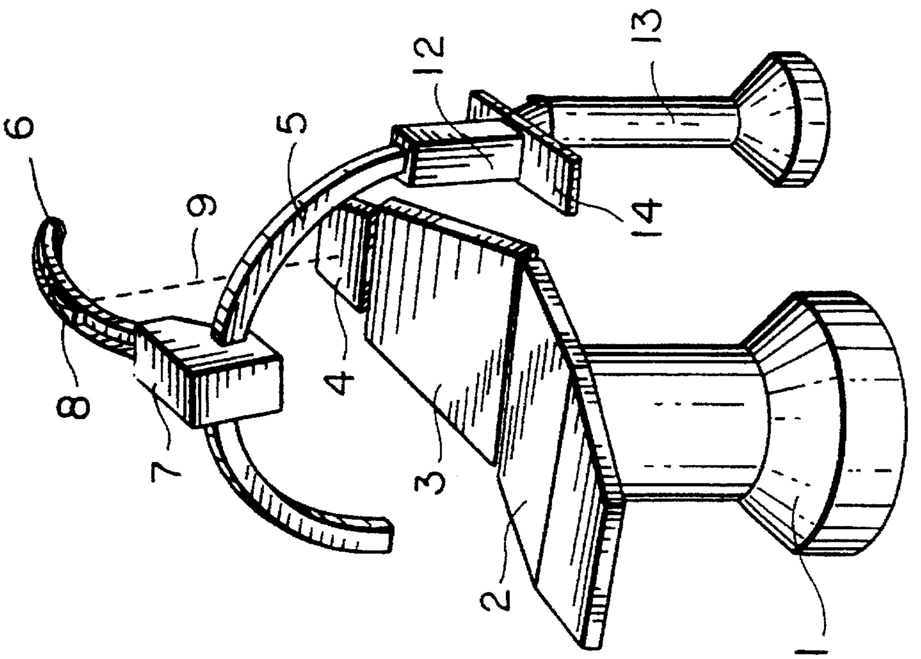
FIG. 2 shows correspondingly a second embodiment of the operating lamp device according to the invention.

FIG. 2 shows an alternative embodiment of the operating lamp device according to the invention. Again a treatment chair is shown positioned on a base 1, comprising support section 2, back support 3 and neck support 4. The difference with the embodiment shown in FIG. 1 is, that the guiding apparatus, which again comprises a first arc-shaped guide 5 having a first slide 7 and a second arc-shaped 6 having a second slide 8, is not attached anymore to the back support of the treatment chair, but to a separate carrier 13. As is the base 1 this carrier is able to be adjusted in height, while at its top a pivoting support 14 is provided. The pivot axis between the carrier 13 and the support 14 generally always coincides with the pivot axis between the support section 2 and back section 3 of the treatment chair.

Now the height adjustment guide 12 is attached to the support 14, and, as mentioned before, adjustably houses the first arc-shaped guide 5. Further the height adjustment guide 12 is able to be adjusted in the longitudinal direction of the support 14 (that means in parallel to the longitudinal axis of the treatment chair).

The treatment chair contains motion sensors not illustrated further generating control signals in correspondence with the motion of the treatment chair. Thus these control signals define a measure for the position of the treatment chair, for example the height of the support section 2 and the angle between this support section 2 and the back support 3. These control signals are, possibly through a computing section, supplied to a drive for the carrier 13 and support 14 not shown further, such that the support 14 carries out a motion which corresponds with the motion of the back support 3. The result is identical to the result obtained with the embodiment according to FIG. 1; however, now no mechanical coupling occurs between the treatment chair and the guiding apparatus, such that vibrations of the treatment chair (such as during a treatment) will not lead to disturbing vibrations of the light source and the light beam 9 emitted thereby.

The embodiments according to FIGS. 1 and 2 do not show, that the guiding apparatus in its entirity could be moved away from the treatment chair, for example when the height adjustment guide 12 is pivotable around a pivot axis relative to the arm 11 or support 14, respectively, such that a patient can easily step in and out of the treatment chair without being hindered by the guiding apparatus.

It is also possible to mount the guiding apparatus on a second treatment chair positioned alongside the first treatment chair instead of on a carrier 13. Like this also a vibration-free support of the light source is realised. Correspondingly the guiding apparatus may be suspended from the ceiling.

Apart from moving the light source along the guiding apparatus it is preferred too, that the light source may be adjusted relative to the guiding apparatus according to a radian of the spherical cap as defined by the guiding apparatus. This means, that the light source in a way can be moved along the light beam 9 emitted by it towards or away from the treatment area. Due to such an adjustment the light intensity at the treatment area may be varied.

Figure 3:
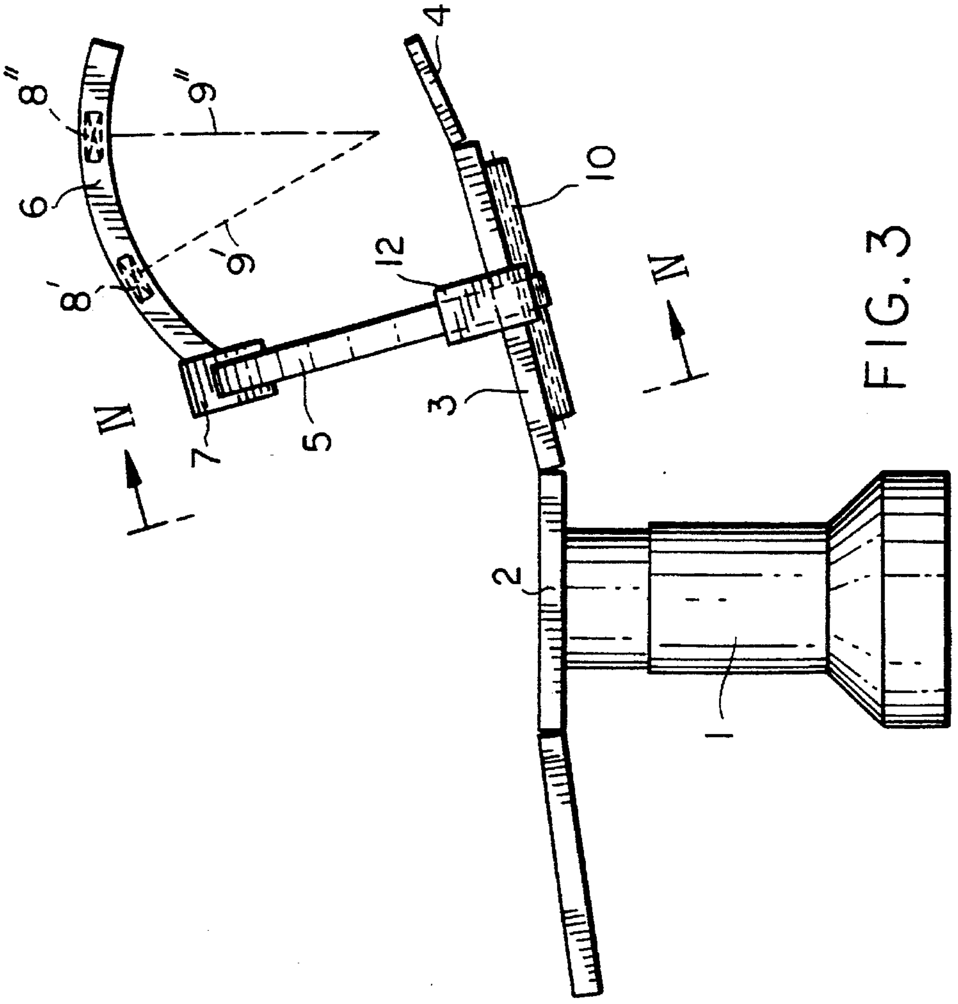
FIG. 3 shows a side elevational view of the embodiment shown in FIG. 1.

FIG. 3 shows in a side elevational view again the embodiment illustrated in FIG. 1. The second slide 8 (comprising the light source, not illustrated) is indicated in two positions 8' and 8" with corresponding light beams 9' and 9". The intersection of both light beams coincides with the treatment area of the patient.

The direction of the light beam 9' is fit for treatments at the upper jaw of a patient, for this light beam in a way comes from below relative to the treatment area of the patient. Correspondingly light beam 9" is more appropriate for treatments at the lower jaw of a patient. Now it is conceivable, that the motion of the second slide 8 from position 8' towards position 8" and backward is automatically controlled by an angular sensor, which determines the angle between the support section 2 and the back support 3. This applies because a treatment at the upper jaw of a patient generally will require a small angle between the support section 2 and the back support 3, for example as illustrated in FIG. 3. In such a position the slide is at position 8'. If however a treatment at the lower jaw of a patient occurs, the angle between back support 3 and support section 2 will increase, such that the angular sensor generates a corresponding signal and the slide will be displaced automatically towards position 8". Thus in correspondence with the angle between the back support 3 and the support section 2 the chair determines itself what angle of attack the light beam 9 should have at the treatment area.

Figure 4:
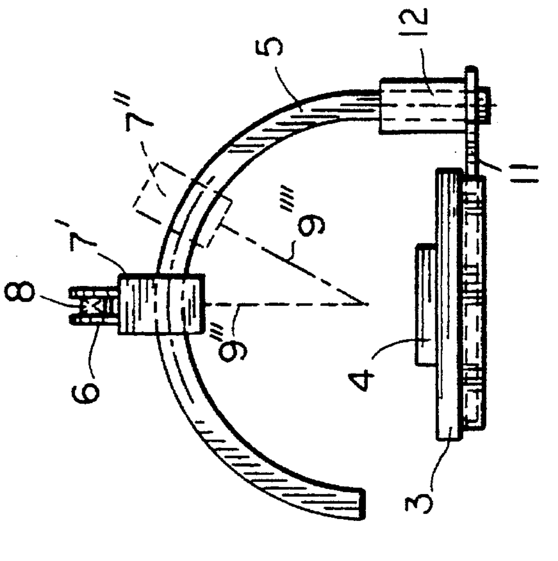
FIG. 4 shows a view along line IV—IV in FIG. 3.

FIG. 4 illustrates a section according to line IV—IV in FIG. 3. One can see, that during a displacement of the first slide from position 7' towards position 7" the light beams 9''' and 9"" emitted by the light source go through an intersection which again coincides with the treatment area.

The invention is not limited to the embodiments described before, which can be varied widely within the scope of the invention as defined by the claims.

I claim:

1. Operating lamp device comprising a light source and means for directing a light beam emitted by said light source towards a pre-determined treatment area of a patient lying on an operating table or sitting in a treatment chair and for maintaining the light beam on said treatment area during a movement of said operating table or treatment chair, characterised in that the means comprise a guiding apparatus for the light source, which has a stationary position relative to the operating table or treatment chair and which offers to said light source a spherical cap-shaped area of movement, wherein the centre of curvature of the spherical cap coincides with the treatment area of the patient, and the light source being provided with proximity switches for causing a motion of the light source along the guiding apparatus.

2. Device according to claim 1, characterised in that the guiding apparatus is attached to a movable back support or neck support of the operating table or treatment chair.

3. Device according to claim 1, characterised in that the guiding apparatus is attached to a separate carrier not mechanically coupled with the operating table or treatment chair, said carrier being movable in correspondence with the movement of the operating table or treatment chair under influence of control signals generated by motion sensors in said operating table or treatment chair.

4. Device according to claim 1, characterised in that the guiding apparatus is adjustable relative to the operating table or treatment chair.

5. Device according to claim 1, characterised in that the guiding apparatus is able to be moved away, such as to be pivoted away, from the operating table or treatment chair.

6. Device according to claim 1, characterised in that the guiding apparatus comprises a first arc-shaped guide extending transversally to the longitudinal direction of the operating table or treatment chair and a second arc-shaped guide movable along said first arc-shaped guide and extending into the longitudinal direction of the operating table or treatment chair, wherein the light source is able to move along said second arc-shaped guide.

7. Device according to claim 1, characterised in that the light source is adjustable relative to the guiding apparatus along a radian of the spherical cap.

8. Device according to claim 1, characterised in that the light source is automatically movable along the guiding apparatus dependent upon the position of the operating table or treatment chair.

* * * * *